the translation motion is in the plane of the film and is such that a predetermined offset point on the film is caused to move along a circular path having the intersection of the crystal axis and the film plane as its center. The additional motion of the film results in a photograph having concentric annuli of given width formed by the diffraction spots from successive levels of the reciprocal lattice. The distance between the chosen offset point and the crystal axis intersection point determines the width of the annuli, and the offset point may be chosen at any point on the film which is within a circle having the crystal axis intersection point as its center and having a radius equal to the distance between the crystal axis intersection point and the beam axis intersection point. One embodiment of the resolving cone axis camera is described wherein the film holder which imparts the translation motion to the film consists of three parallel interleaved plates wherein the second plate is free to move horizontally with respect to the first plate and the third plate to which the film is attached, is free to move vertically with respect to the second plate. A circular cam whose center is offset from the crystal axis rotates eccentrically about the crystal axis and provides the third plate and the film thereon with the desired translation motion.

United States Patent [19]

Donnay et al.

[11] 4,015,125
[45] Mar. 29, 1977

[54] RESOLVING CONE-AXIS CAMERA

[75] Inventors: Gabrielle Donnay, Montreal; Yvon Le Page, Brossard, both of Canada

[73] Assignee: Canadian Patents and Development Limited, Ottawa, Canada

[22] Filed: Nov. 17, 1975

[21] Appl. No.: 632,849

[30] Foreign Application Priority Data

Feb. 28, 1975 Canada .............................. 221018

[52] U.S. Cl. ............................... 250/275; 250/274
[51] Int. Cl.$^2$ ...................................... G01N 23/20
[58] Field of Search ........... 250/272, 273, 274, 275

[56] References Cited
UNITED STATES PATENTS

| | | | |
|---|---|---|---|
| 3,108,185 | 10/1963 | Buerger | 250/275 |
| 3,848,126 | 11/1974 | Swindells et al. | 250/275 X |
| 3,903,415 | 9/1975 | Holzapfel | 250/272 |

Primary Examiner—Archie R. Borchelt
Attorney, Agent, or Firm—Edward Rymek

[57] ABSTRACT

A resolving cone-axis camera which imparts an additional translation motion to the film as the diffraction spots from the precessing crystal impinge upon the 8 Claims, 10 Drawing Figures

RESOLVING CONE-AXIS CAMERA

The present invention relates to crystallography instruments and in particular to a resolving cone-axis camera for producing cone-axis photographs of a crystal simultaneously at the zero level and other successive levels of the reciprocal lattice.

Various crystallography cameras have been developed over the years. In one particular type, the crystal and film are interconnected so as to maintain the plane of the film parallel to the plane of the reciprocal lattice of the crystal at all times while the crystal precesses about the axis of the X-ray beam. In one such instrument, the cone-axis camera, the film is rigidly connected to the crystal and precesses with it such that the axis of the crystal is normal to the film and intersects the film plane at one fixed point at all times. This instrument produces photographs having a number of narrow concentric Laue circles which represent successive levels of the reciprocal lattice. The diffraction spots, however are so crowded on the concentric circles that they have not been usable for data collection.

A practical form of the instrument which was therefore developed, is described in detail in the text — The Precession Method by Martin J. Buerger, 1964, John Wiley & Sons Ltd., Library of Congress Catalog Card Number 64-23830 - Chapter 4, pages 30 to 43. In this instrument, which is known as a precession camera, the crystal and film are each supported by duplicate gimbal type supports which are interconnected such that each individually precesses about the X-ray beam axis is unison. The diffraction spots for one level of the reciprocal lattice are thus spread out on the film, which facilitates the reading of the film by densitometer measurements, however, a separate photograph is required to record the diffraction spots for each level of the reciprocal lattice. Problems therefore arise in that the films must be developed under identical conditions to obtain comparable readings and, in addition, the lengthy exposure time of the crystal to X-rays often deteriorates the crystal during data collection.

It is therefore an object of this invention to provide an apparatus for producing on a single photograph the diffraction spots of the various levels of the reciprocal lattice which may be readily used for data collection.

It is a further object of this invention to provide an apparatus for producing a readable cone axis photograph of the various levels of the reciprocal lattice of a crystal.

These and other objects are achieved in a resolving cone-axis camera which imparts an additional translation motion to the film as the diffraction spots from a precessing crystal impinge upon the film. This translation motion is in the plane of the film and is such that a predetermined offset point on the film is caused to describe a circular path having the intersection of the crystal axis and the film plane as its center. The additional motion of the film results in a photograph having concentric annuli of given width formed by the diffraction spots from successive levels of the reciprocal axis. The distance between the chosen offset point and the crystal axis intersection point determines the width of the annuli, and the offset point may be chosen at any point on the film which is within a circle having the crystal axis intersection point as its center and having a radius equal to the distance between the crystal axis intersection point and the beam axis intersection point.

Figure 1:
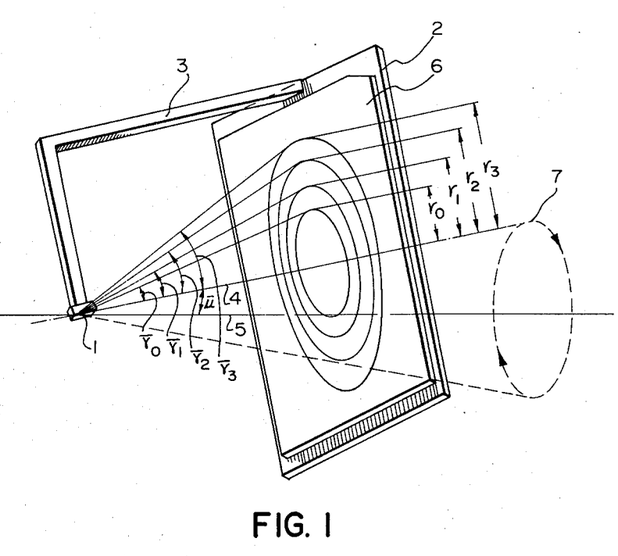
FIG. 1 is a schematic illustration of the principle of a cone-axis camera.
Figure 2:
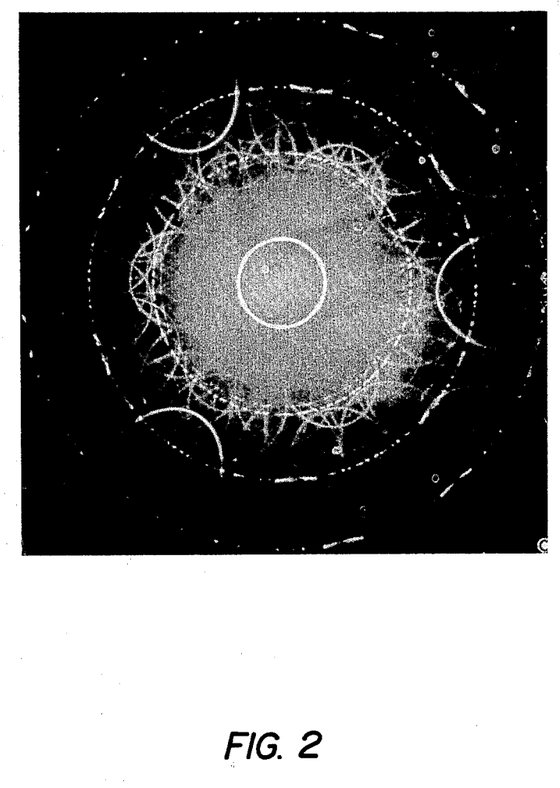
FIG. 2 illustrates a typical cone-axis photograph.

Referring to FIG. 1, in a cone-axis camera, a crystal 1 is rigidly connected to a back plate 2 by an arm 3 such that the reciprocal lattice plane of the crystal 1 is parallel to the back plate 2 upon which a film 6 is attached. The crystal axis 4 is therefore normal to the plane of the film 6. The crystal is mounted in an x-ray beam such that the crystal axis 4 is at an angle $\bar{\mu}$ to the x-ray beam 5. In operation, the crystal is given a precessing motion about the axis 5 such that the crystal axis 4 follows an imaginary cone 7 having the x-ray beam axis 5 as its axis and having an angle $\bar{\mu}$. The crystal 1 is thus at the apex of cone 7. As the crystal precesses about axis 5, the various levels of the reciprocal lattice diffract the x-ray beam such that diffraction spots appear on the film 6 in concentric circles to produce a cone-axis photograph. The inner circle or zero-order cone is produced at an inclination angle $\bar{\nu}_o$ to the crystal axis 4 and has a radius $r_o$, the inclination angle $\bar{\nu}_o$ being equal to the precession angle $\bar{\mu}$. The other concentric circles are produced by the 1st, 2nd, 3rd . . . levels of the crystal lattice at an angle $\bar{\nu}_1, \bar{\nu}_2, \bar{\nu}_3, \ldots$ to the crystal axis and have a radius of $r_1, r_2, r_3, \ldots$ respectively. An example of a typical cone-axis photograph is shown in FIG. 2 wherein levels 0 (nearest the center), 1, 2 and 3 are shown for a tourmaline crystal taken at a precession angle of 10° with molybdenum unfiltered K radiation excited at 40 kV. As can be seen in FIG. 2, the diffraction spots are so crowded on the concentric circles that they are not usable for data collection since they cannot be properly indexed, nor their intensities measured.

The resolving cone-axis camera in accordance with this invention spreads each concentric circle into an annulus of a given width, recording all diffractions obtainable from the zero and upper levels on a single film so that they can be indexed and their intensities measured. This is achieved by providing an additional motion to the film in the plane of the film, as shown schematically in FIG. 3.

Figure 3:
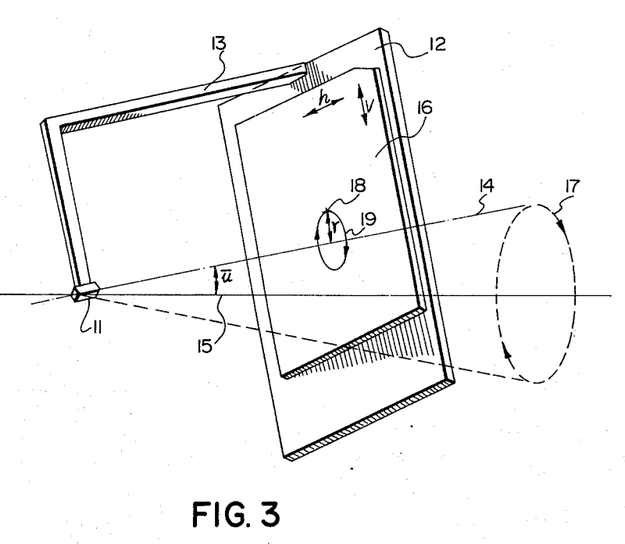
FIG. 3 is a schematic illustration of the principle of the resolving cone-axis camera in accordance with this invention.

As in FIG. 1, a crystal 11 is rigidly connected to a back plate 12 by an arm 13 such that the reciprocal lattice plane of the crystal is parallel to the back plate 12 and the crystal axis 14 is normal to the plane of the back plate 12. The crystal is mounted in the path of an x-ray beam such that the crystal axis 14 is at an angle $\bar{\mu}$ to the x-ray beam axis 15. Also as in FIG. 1, this arrangement is driven to provide the crystal 11 with a precessing motion about the axis 15 such that the crystal axis 14 generates an imaginary cone 17 having the x-ray beam axis 15 as its axis and having an angle $\bar{\mu}$. In accordance with this invention however, the film 16 which is parallel to the back plate is provided with a translation motion in two dimensions $h$ and $v$ with respect to the backplate 12. In order to spread the diffraction spots recorded on the film 16, the film 16 is given a motion such that every point on the film describes a circle of a given radius $r$ and that a predetermined point 18 on the plane of the film 16, which is offset from the crystal axis 14 by a distance $r$, describes a circle 19 having the crystal axis 14 as its axis. In addition, the film 16 motion is synchronized with the crystal 11 precession motion in a 1:1 ratio such that these motions have cycles of equal time span, i.e. for each complete turn of the axis 14 about cone 17, offset point 18 describes one complete circle about the axis 14.

Figure 4:
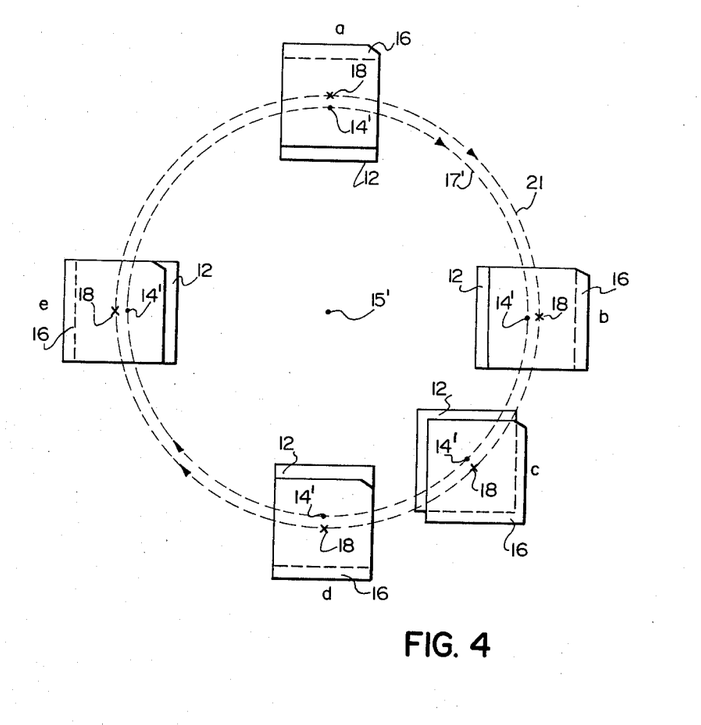
FIG. 4 is an illustration of the relative position of the film at five points during the crystal precession cycle.

The relative position of the film 16 with respect to the backplate 12 at five positions $a$, $b$, $c$, $d$, and $e$, during one complete cycle of the apparatus is shown schematically in FIG. 4. The x-ray beam axis 15 is normal to the plane of drawing and intersects with the drawing at point 15′, and the crystal axis 14 extends from the crystal on the x-ray beam axis through an intersection point 14′. In operation, as the crystal axis 14 generates a cone about the x-ray beam axis 15, point 14′ moves along a circular path 17′ in the clock-wise direction. Point 14′ is shown $a$ — at 0°, $b$ — at 90°, — at 135°, $d$ — at 180°, $e$ — at 270° and back to $a$ at 360° for one cycle. As the backplate 12 moves through one cycle, the offset point 18 moves in a circular path about point 14′ and is directly above 14′ in $a$, to the right of 14′ in $b$, below 14′ in $d$ and to the left of 14′ in $e$. Offset point 18 on the film 16 also follows a circular path 20 in the clockwise direction about point 15′ fixed in space.

Figure 5:
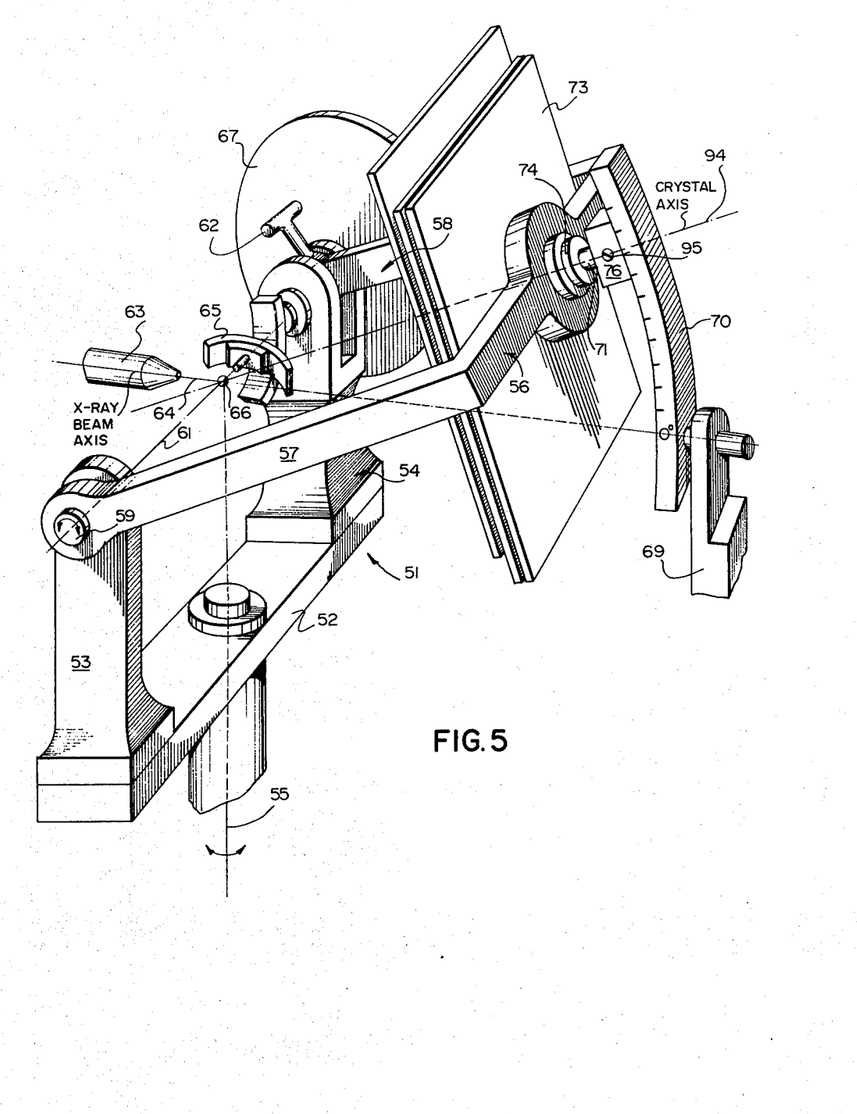
FIG. 5 is a perspective view of one embodiment of the resolving cone-axis camera in accordance with this invention.
Figure 6:
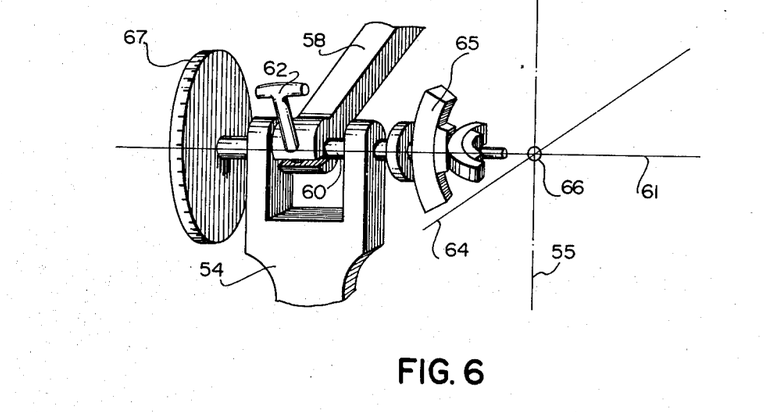
FIG. 6 is a view of the crystal holding mechanism.
Figures 7, 8:
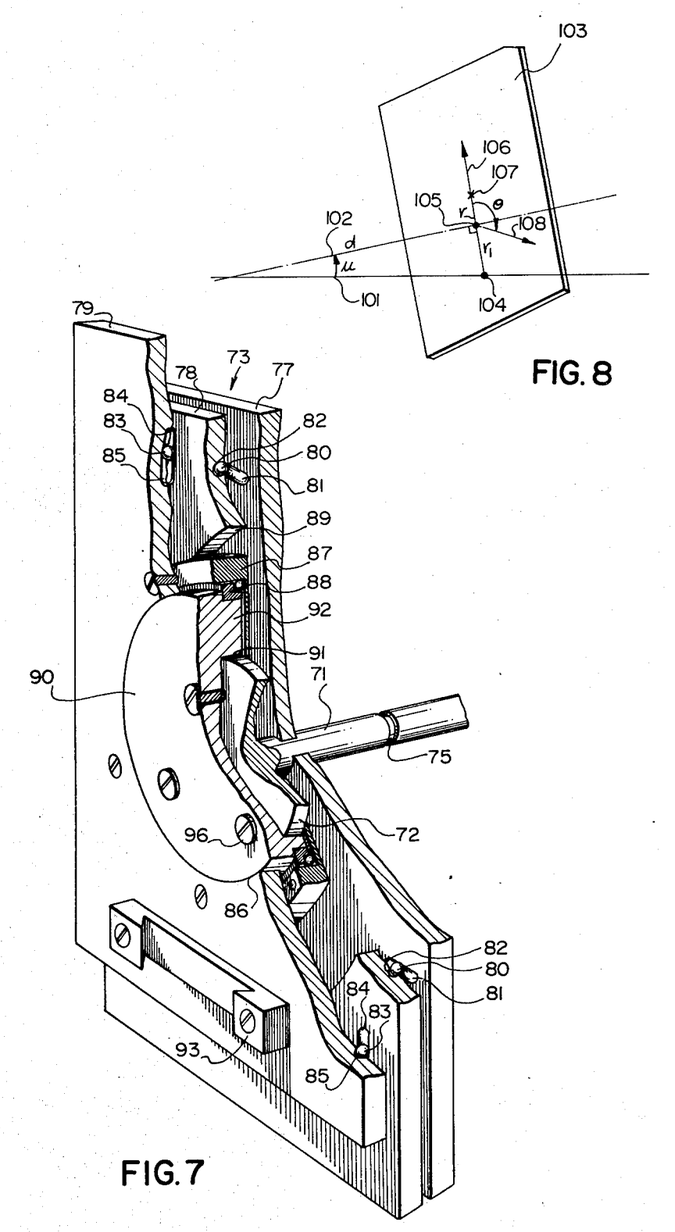
FIG. 7 is a view of the film holding mechanism.
FIG. 8 is a schematic illustration of the translation motion of the film.

One embodiment which a resolving cone-axis camera in accordance with this invention may take, is shown in FIGS. 5, 6 and 7, wherein FIG. 5 illustrates the cone-axis camera mechanism generally, FIG. 6 illustrates the crystal holding mechanism and FIG. 7 illustrates the film holding mechanism in detail.

The camera 51 includes a gimbal 52 which has two arms 53 and 54. The gimbal 52 is mounted on a base (not shown) such that it rotates freely about a vertical axis 55. A U-shaped film holder support structure 56 has arms 57 and 58 connected to arms 53 and 54 respectively by means of shafts 59 and 60 respectively such that the arms 57 and 58 rotate freely about a horizontal axis 61. A locking device 62 is used to rigidly connect the arm 58 to shaft 60 such that they will rotate as a unit. An x-ray source, only the collimator 63 of the source being shown, is mounted so that the x-ray beam axis 64 passes through the intersection of axes 55 and 61. A goniometer head 65 is mounted on the end of shaft 60 so as to rotate with shaft 60. The goniometer head 65 is used to hold a crystal 66 and adjust its position vertically and horizontally at the intersection of axes 55 and 61. A graduated circle 67 is mounted on the end of shaft 60 and is used to adjust the angle of the crystal 66 in such a way that the crystal axis 94 is normal to the plane of the film attached to the film holder to be described.

The precession drive mechanism for the camera consists of a motor driven shaft 68 which is supported in a base 69 (partially shown) such that the shaft 68 axis coincides with the x-ray beam axis 64. An arc 70 graduated in degrees is fixed to the shaft 68 so as to rotate with it. A further shaft 71 having a flat circular head 72 passes through the film holder mechanism 73, the base of the U-shaped support 56 and a bearing member 74 in such a manner that the axis of shaft 71 coincides with the crystal axis 94 when the crystal axis 94 is normal to the plane of the film on holder 73. The bearing member 74 is fixed by screws or bolts to support 56 and includes an O-ring and a snap ring that fits in a groove 75 on the shaft 71 to hold it snugly while allowing it to rotate freely. The end of shaft 71 is fixed to an element 76, as by a screw 95, and element 76 is movably mounted on the arc 70 to adjust the camera 51 to the desired precession angle $\bar{\mu}$, i.e. the angle between the x-ray beam axis 64 and the crystal axis 94.

The film holder mechanism 73 includes three plates, the backplate 77 which is fixed to the base of the U-shaped support 56, the second plate 78 which moves freely in the horizontal direction with respect to the backplate 77 and the third plate 79 which moves freely in the vertical direction with respect to the second plate 78. In the present embodiment, plates 77 and 78 are separated by a ball-bearing 80 in each corner which roll in horizontal grooves 81 and 82 in plates 77 and 78. Plates 78 and 79 are separated by a ball-bearing 83 in each corner which roll in vertical grooves 84 and 85 in plates 78 and 79. An annular ball-bearing structure consisting of an inner race 88 of L-cross-section and an outer race 87 of L-cross-section is fixed to plate 79 concentrically with a circular opening 86 therein. Plate 78 also includes circular opening 89 with a diameter greater than the diameter of the annular ring 87. The translation motions of plates 78 and 79 with respect to plate 77 are imparted to the plates by means of a cam 90 having a diameter such that it fits snugly within opening 86 in plate 79. Cam 90 includes a circular recess 91 machined therein which is mounted over head 72 on shaft 71 and secured to it by screws 96. Cam 90 further has an annular groove 92 on its outer edge which fits over the inner race 88 of the ball bearing structure. The center of the cam 86, which is the offset point, is offset from the center of recess 91 by a predetermined distance. This offset distance determines the desired width of the concentric annulus for each level of the photographed diffracted spots, i.e. the greater the offset between the centers, the greater the width of each annulus, since as shaft 71 and thus, cam 90 rotate, the offset point at the center of the cam 90 and therefore, a corresponding point on the film moves in a circular motion about the axis of shaft 71. The film which is used to record the diffraction spots is mounted on plate 79 in any conventional manner. This may take the form of a cassette which slips into a pair of brackets 93.

In the above description with respect to FIGS. 3 to 7, the initial film offset has been shown as being in the plane of the film in the direction of a line which starts on the x-ray beam axis and extends through the crystal axis. This is shown schematically in FIG. 8, where the x-ray beam axis 101 and the crystal axis 102 are projected onto the plane of a film 103 at intersection points 104 and 105 respectively. A line 106 starts at point 104 and extends through point 105. The film 103 being offset in the direction of line 106 such that the offset point 107 falls on the line 106, a distance $r$ from point 105, i.e. at an angle of 0° to line 106. However, as can be seen in FIG. 7, the cam 90 may be mounted on the shaft head 72 such that the center of cam 90, the offset point, is offset at some other angle $\theta$ subtended about the crystal axis. This may be done by rotating cam 90 with respect to shaft head 72 before securing the two together, or by rotating the shaft 71 with respect to element 76 (FIG. 5) before it is fixed to element 76 by screw 95. This is shown schematically in FIG. 8 wherein the offset point 107 may be on a line 108 through point 105 at any angle $\theta$ with respect to line 106, where $0 < \theta < 360°$.

Figure 9:
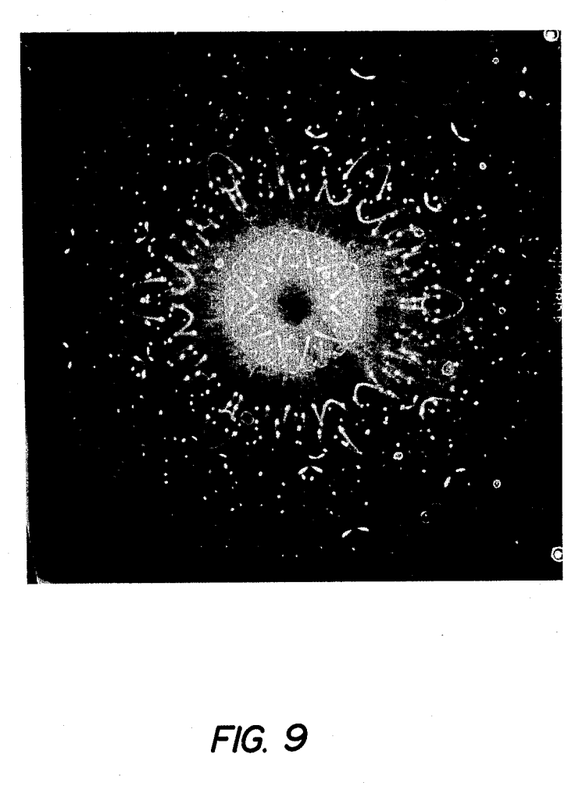
FIG. 9 is a photograph of the annuli when the offset point is at an offset angle of 0°.

FIG. 9 illustrates a diffraction diagram which was obtained by a resolving cone-axis camera in accordance with this invention, of the same tourmaline cyrstal used to obtain FIG. 2. Once again, a 10° precession angle and molybdenum unfiltered K radiation was used. The offset angle $\theta$ was fixed at 0°. The offset distance $r$, the distance between the center of the cam 90 and the center of the shaft head 72, was fixed at 6 mm which spread each circle into annuli of width 12 mm.

Figure 10:
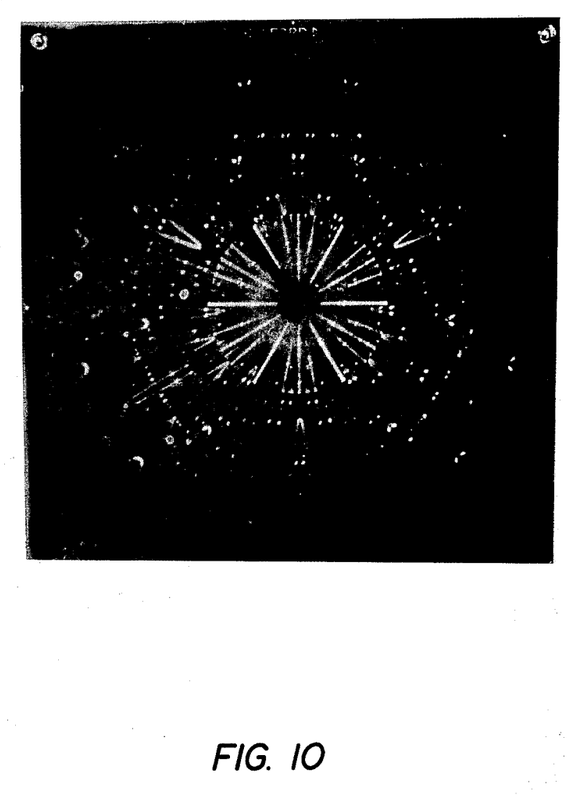
FIG. 10 is a photograph of the diffraction spots when the offset point is at the intersection of the x-ray beam axis and the film plane.

In addition, when the offset angle $\theta = 180°$, and when $\tan \bar{\mu} = r^1/d$ where $\bar{\mu}$ is the precession angle, $r^1$ is the distance between the x-ray beam axis 101 and the crystal axis 102 on the surface of the film, and $d$ is the distance from the crystal to the film 103, i.e. when the offset point is on the intersection of the x-ray beam axis 101 and the film plane, the resulting diffraction diagram for the tourmaline crystal will be of the type shown in FIG. 10 wherein the circles are spread in such a way that the zero level gives a precession pattern which is similar to the pattern obtained by instruments described in the text by Martin J. Buerger, on The Precession Method which has been cited above.

We claim:

1. In a cone axis camera for recording the diffraction spots from successive levels of the reciprocal lattice of a crystal on a film, means for providing the film with a predetermined translation motion in the plane of the film such that said diffraction spots are recorded on said film in concentric annuli having a given width.

2. In a cone axis camera having a crystal holder means for precessing a crystal about an x-ray beam axis to produce diffraction spots from successive levels of the reciprocal lattice of the crystal which are recorded on a film that is mounted in a film holder which maintains the film parallel to the reciprocal lattice of the crystal at a fixed distance from the crystal along the crystal axis:

means for providing a predetermined offset point on said film with an additional translation motion in the plane of the film such that said offset point follows a circular path which has the crystal axis as its center.

3. In a cone axis camera as defined in claim 2 wherein said offset point lies on a line in the plane of the film which starts at the intersection of x-ray beam axis and the film plane and extends through the crystal azis and the film plane.

4. In a cone axis camera as defined in claim 3 wherein said offset point lies at the intersection of the x-ray beam axis and the film plane.

5. A resolving cone axis camera for recording x-ray diffraction spots from successive levels of the reciprocal lattice of a crystal on a film comprising:

means for holding the crystal on the x-ray beam axis;

means connected to the crystal holding means for precessing the crystal about the x-ray beam axis at a precession angle $\bar{\mu}$; and means rigidly connected to the crystal holding means for maintaining the film a fixed distance from the crystal along the crystal axis and parallel to the plane of the reciprocal lattice of the crystal as the crystal precesses about the x-ray beam; and means for providing the film with a translation motion in the plane of the film such that said diffraction spots are recorded on said film in concentric annuli having a given width.

6. A resolving cone axis camera as claimed in claim 5 wherein said translation motion means drives a predetermined point on the film which is offset from the crystal axis in a circular path about the crystal axis.

7. A resolving cone axis camera as claimed in claim 6 wherein said translation motion means further provides said predetermined point on the film with a circular path about the x-ray beam axis.

8. A resolving cone axis camera for recording x-ray diffraction spots from successive levels of the reciprocal lattice of a crystal on a film comprising:

means for holding a crystal on the x-ray beam axis;

means connected to the crystal holding means for precessing the crystal about the x-ray beam axis at a precession angle $\bar{\mu}$;

first plate means connected to said precessing means such that said plate means is maintained parallel to the plane of the reciprocal lattice of the crystal at a fixed distance from the crystal along the crystal axis;

second plate means positioned parallel to said first plate means, for holding said film, said second plate means having a predetermined offset point thereon;

means for providing said second plate means with a translation motion with respect to said first plate means such that said predetermined offset point moves along a circular path about the crystal axis.

* * * * *